United States Patent [19]
Andress, Jr.

[11] 3,969,237
[45] July 13, 1976

[54] LUBRICANT COMPOSITIONS CONTAINING BENZOTRIAZOLE DERIVATIVES AS COPPER PASSIVATORS

[75] Inventor: Harry J. Andress, Jr., Pitman, N.J.

[73] Assignee: Mobil Oil Corporation, New York, N.Y.

[22] Filed: Jan. 4, 1974

[21] Appl. No.: 430,870

Related U.S. Application Data

[63] Continuation-in-part of Ser. No. 344,007, March 22, 1973, abandoned.

[52] U.S. Cl. .............................. 252/49.9; 252/32.5; 252/51.5 A; 252/389 A; 252/392
[51] Int. Cl.² ........................................ C10M 1/10
[58] Field of Search ............... 252/32.5, 34, 49.9, 252/51.5 A, 389 A, 392 TD

[56] References Cited
UNITED STATES PATENTS

| | | | |
|---|---|---|---|
| 3,697,427 | 10/1972 | Byford et al. | 252/49.9 |
| 3,778,376 | 12/1973 | Herber | 252/49.9 X |
| 3,803,047 | 4/1974 | Hwa | 252/389 A |
| 3,816,428 | 6/1974 | Redmore | 252/392 X |
| 3,819,647 | 6/1974 | Foley | 252/32.5 X |
| 3,846,317 | 11/1974 | Lintzenich | 252/49.9 X |

*Primary Examiner*—Delbert E. Gantz
*Assistant Examiner*—Andrew H. Metz
*Attorney, Agent, or Firm*—Charles A. Huggett; Raymond W. Barclay

[57] ABSTRACT

Organic compositions, which are normally susceptible of corroding copper, are provided, containing, in an amount sufficient to inhibit such corrosion, benzotriazole derivatives said derivatives having been prepared by reacting (A) benzotriazole and (B) a reactant selected from the group consisting of hydrocarbyl carboxylic acids having at least 18 carbon atoms, mono and di-substituted organic phosphates, and mono and di-substituted phosphonates wherein the organic substituent contains at least 15 carbon atoms and wherein said reaction is conducted at a temperature from about 100°C to about 200°C and in a mole ratio of (A) to (B) from about 1:1 to about 1:0.5.

14 Claims, No Drawings

LUBRICANT COMPOSITIONS CONTAINING BENZOTRIAZOLE DERIVATIVES AS COPPER PASSIVATORS

CROSS REFERENCE TO RELATED APPLICATIONS

Continuation-in-part of application Ser. No. 344,007, filed Mar. 22, 1973 and now abandoned.

BACKGROUND OF THE INVENTION

1. Field of the Invention

This invention relates to improved organic compositions and, in one of its aspects, relates more particularly to improved organic compositions in the form of liquid and solid hydrocarbon-containing materials which normally tend to react with and corrode copper surfaces under conditions of use. Still more particularly, in this aspect, the invention relates to improved organic compositions in the form of lubricating oils, greases, fuels and solvents, which in their uninhibited state, tend to react with and corrode copper surfaces with which they may come into contact in performing their intended function.

2. Description of the Prior Art

Prior to the present invention, attempts have been made to employ benzotriazole in gear oils as a copper corrosion inhibitor. In such applications, it has been found that because of the very limited solubility of benzotriazole in mineral base oils, dissolution of the benzotriazole can only be carried out to a very small extent and only if the benzotriazole is first dissolved in a suitable solvent. In instances where relatively higher concentrations are required for combating extensive degrees of corrosion susceptibility, such increased concentration of the benzotriazole in the hydrocarbon medium, is not feasible. The prior art has suggested several methods by which the solubility of benzotriazole can be enhanced. These methods, for the most part, comprise either alkylating the aromatic nucleus of the benzotriazole or incorporating another functional group in this nucleus. Each of these methods, although feasible, was accomplished only with great difficulty and was associated with low yields.

SUMMARY OF THE INVENTION

In accordance with the present invention, improved organic compositions, which are normally susceptible of corroding copper, are provided, containing, in an amount sufficient to inhibit such corrosion, the reaction product of benzotriazole and a reactant selected from the group consisting of carboxylic acids having at least 18 carbon atoms, and mono and di-substituted organic phosphates and mono and di-substituted organic phosphonates, wherein the organic substituent contains at least 15 carbon atoms, as more fully hereinafter described. These reaction products are found to be more soluble in hydrocarbon media than benzotriazole and to be effective corrosion inhibitors. Thus, it is found that these reaction products are markedly effective as corrosion inhibitors in such organic media as gasoline, jet fuels, fuel oil, solvents, gear oils, hydraulic oils, turbine oils, cutting oils and greases. These reaction products may be incorporated in any amount effective for inhibiting the degree of corrosion susceptibility of the organic composition. In most applications, the reaction product is generally employed in an amount from about 0.001 to about 1 percent, and, preferably, in an amount from about 0.1 to about 0.5 percent, by weight, of the total organic composition. In general, the reaction between the benzotriazole and the reactant is carried out in a mol ratio of from about 1:1 to about 1:0.5. The reaction is carried out at a temperature from about 100°C. to about 200°C., and, preferably at a temperature from about 125°C. to about 175°C. Representative of the carboxylic acids employed for reaction with the benzotriazole are oleic acid, dimer acids and trimer acids. Dimer acid is produced by the polymerization of unsaturated fatty acids at mid-molecule and is a dibasic acid of high molecular weight and relatively long alkyl chains between its carboxyl groups. In contrast to other dibasic acids, dimer acid is a liquid. Commercial grades of dimer acids are actually mixtures of dimer acid (a $C_{36}$ dibasic acid), trimer acid (a $C_{54}$ tribasic acid) and small residual amounts of $C_{18}$ monobasic acid. Representative of the mono and di-substituted organic phosphates employed for reaction with the benzotriazole are mono (nonylphenyl) phosphates and di (nonylphenyl) phosphates. Representative of the mono and di-substituted organic phosphonates employed for reaction with the benzotriazole are mono (nonylphenyl) and di (nonylphenyl) phosphonates.

A field of specific applicability of the present invention is in the improvement of organic liquid compositions in the form of petroleum distillate fuels and oils. These distillate fuels and oils are not restricted to straight-run fuels and oils and can comprise straight-run distillates, catalytically or thermally cracked (including hydrocracked) distillate fuels or mixtures of straight-run distillate fuel oils, naphthas and the like, with cracked distillate stocks. Moreover, such fuels and oils can be treated in accordance with well-known commercial methods, such as acid or caustic treatment, hydrogenation, solvent refining, clay treatment and the like.

Particularly contemplated, among the fuels and fuel oils are those boiling in the gasoline range, jet fuels domestic fuel oils, such as Nos. 1, 2 and 3 fuel oils, used in heating and as diesel fuel oils and turbine fuels. The domestic fuel oils generally conform to the specifications set forth in ASTM Specification D396-48T. Specifications for diesel fuels are defined in ASTM Specification D975-48T. Typical jet fuels are defined in Military Specification MIL-F-5624B. Also included are gear oils, hydraulic oils and cutting oils.

In another field of specific applicability, the organic compositions improved in accordance with the use of the reaction products of the present invention, include any of the conventional hydrocarbon oils of lubricating viscosities which are capable of corroding copper. These may include mineral or synthetic lubricating oils, aliphatic phosphates, esters and diesters, silicates, siloxanes, oxalkyl ethers or esters. Mineral lubricating oils employed as the lubricating composition may be of any suitable lubricating viscosity and may range from about 45 SSU to about 6,000 SSU at 1000°F., and preferably from about 50 SSU to about 250 SSU at 210°F. These oils may have viscosity indexes from below 0 to about 100 or higher. Viscosity indexes from about 70 to about 95 are preferred. The average molecular weight of these oils may be, for example, from about 250 to about 800.

As hereinbefore indicated, the aforementioned reaction products may also be incorporated as anti-corrosion agents for copper in grease compositions. Such greases may comprise a combination of a wide variety of lubricating vehicles and thickening or gelling agents. Thus, greases in which the aforementioned reaction products are particularly effective may comprise any of the aforementioned conventional hydrocarbon oils of lubricating viscosity as the oil vehicle, and may include any of the aforementioned mineral or synthetic lubricating oils of the type indicated.

With respect to the formation of improved grease compositions in which the aforementioned reaction products are to be incorporated, the choice of employing a mineral or a synthetic oil of lubricating viscosity can best be determined from the nature of the intended environmental use for the grease. Thus, when high-temperature stability is not a requirement of the finished grease, mineral oils having a viscosity of at least 40 SSU at 100°F., and particularly, those falling within the range from about 60 SSU to about 6000 SSU at 100°F. may be effectively employed. In instances where synthetic vehicles are employed, rather than mineral oils, or in combination therewith as the lubricating vehicle, various compounds of this type may be successfully utilized. Typically, synthetic vehicles include: polypropylene, polypropylene glycol, trimethylol propane esters, neopentyl and pentaerythritol esters, di-(ethyl hexyl) sebacate, di-(2-ethyl hexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes (poly-siloxanes), alkyl-substituted diphenyl ethers exemplified by a butyl-substituted bis(p-phenoxy phenyl) ether, phenoxy phenyl ethers, etc.

The lubricating vehicles of the aforementioned improved greases of the present invention containing the reaction product additive, are combined with a grease-forming quantity of a thickening agent. For this purpose, a wide variety of materials may be employed. These thickening or gelling agents may include any of the conventional metal salts or soaps which are dispersed in the lubricating vehicle in grease-forming quantities in such degree as to impart to the resulting grease composition the desired consistency. Other thickening agents that may be employed in the grease formulation may comprise non-soap thickeners, such as surface-modified clays and silicas, aryl ureas, calcium complexes and various other materials. In general, grease thickeners may be employed which do not tend to melt and dissolve when used at the required temperature within a particular environment; however, in all other respects, any material which is normally employed for thickening or gelling hydrocarbon fluids for forming greases, can be used in preparing the aforementioned improved greases in accordance with the present invention.

DESCRIPTION OF SPECIFIC EMBODIMENTS

The following examples will serve to illustrate the preparation of the novel reaction products of the present invention and their efficacy as copper corrosion inhibitors in organic compositions. It will be understood, however, that it is not intended that the invention be limited to the particular inhibitors or the particular organic compositions containing these inhibitors, as described. Various modifications of these inhibitors and organic compositions can be employed, as will readily be apparent to those skilled in the art.

EXAMPLE 1

A mixture of 282 grams (0.1 mol) of oleic acid and 119 grams (1.0 mol) of benzotriazole was stirred at a temperature of about 125°C. for a period of about 3 hours to form a viscous fluid reaction product.

EXAMPLE 2

A mixture of 141 grams (0.25 mol) of dimer acid (comprising 75 percent dimerized linoleic acid and 25 percent trimerized linoleic acid) and 60 grams (0.5 mol) of benzotriazole was stirred for a period of about 4 hours at a temperature of about 150°C. and for an additional period of 4 hours at a temperature of 165°C. to form the resulting reaction product.

EXAMPLE 3

A mixture of 243 grams (0.5 mol) of di(nonylphenyl) phosphonate and 60 grams (0.5 mol) of benzotriazole was stirred at a temperature of 145°C. for a period of about 3 hours to form the resulting reaction product.

EXAMPLE 4

An equimolar mixture of 252 grams (0.62 mols) of mono and di(nonylphenyl) phosphates and 101 grams (0.85 mol) of benzotriazole was stirred at a temperature of 140°C. for a period of 6 hours to form the resulting reaction product.

In order to demonstrate the efficacy of the novel reaction products of the present invention as copper corrosion inhibitors, a base fluid in the form of a gear oil, was first prepared, comprising, by weight: 2% of a sulfur-phosphorous load-support additive containing 31% sulfur and 1.75% phosphorous; 0.25% of di-tertiary-butyl p-cresol; 0.2% polymethacrylate, as a pour depressant; 0.3% silicone defoamant; 0.1% amyl phenyl phosphates; and the balance 20% of a 200 SUS at 100°F. solvent refined paraffinic neutral stock and 80% of a 150 SUS at 210°F. solvent refined paraffinic bright stock.

The above-described base blend was nxt subjected to a series of copper corrosion tests for evaulation employing, in individual tests, the novel reaction products prepared in accordance with the procedures of Examples 1 through 4. The test employed was the standard ASLE 64-9 Wet Corrosion Test. In this test 50 grams of oil sample are placed in a 4 oz. bottle, to which are added 0.5 ml. of distilled water and the contents are vigorously stirred for about one minute. Clean polished pieces of copper are placed in the bottle. The bottle is then stoppered with a cork and placed in an electric drying oven for 24 hours maintaining a temperature of 210° ± 2°F.

In accordance with ASTM D-130 rating, a rating of 1a or 1b denotes a slight tarnish; a rating of 2a, 2b, 2c, 2d and 2e denotes a moderate tarnish; a rating of 3a or 3b denotes a dark tarnish; and a rating of 4a, 4b or 4c denotes corrosion. The individual comparative test results employing the reaction product additives of the present invention are set forth in the following Table I.

Table I

| Test | Compound | | A.S.L.E. 64–9 Wet Corrosion Test Conc.% | Steel | Copper | Sludge |
|---|---|---|---|---|---|---|
| A | Base Fluid | | 0 | Light Stain | 4a | Light |
| B | Base Fluid | + benzo-triazole | 0.1 | Light Stain | 4a | Light |
| C | Base Fluid | + Example 1 | 0.1 | Nil | 1a | Nil |
| D | Base Fluid | + Example 2 | 0.1 | Nil | 1b | Nil |
| E | Base Fluid | + Example 3 | 0.1 | Nil | 1a | Nil |
| F | Base Fluid | + Example 4 | 0.1 | Nil | 1a | Nil |

As will be apparent from the foregoing table, the base fluid of Test A exhibited an unsatisfactory tarnish, particularly with respect to copper in which the rating was 4a. The same base fluid having incorporated thereon 0.1 percent, by weight, of benzotriazole also showed no improvement. On the other hand, the same base fluid, by having incorporated therein 0.1 percent, by weight, of the specific reaction products of Examples 1 through 4 in Tests C through F, respectively, indicated improved and satisfactory results, not only with respect to copper corrosion inhibition but also with respect to steel and sludge.

The above-described base blend was next subjected to a series of tests for evaluation of load-support characteristics, employing, in individual tests, the reaction products prepared in accordance with the procedures of Examples 1 through 4. The test employed was the standard Timken O.K. Load Test. The results obtained are set forth in the following Table II.

Table II

| Test | Compound | | Timken O.K. Load Test Conc.% | Load Pounds/Sq. In. |
|---|---|---|---|---|
| A | Base Fluid | | 0. | 45 |
| B | Base Fluid | + benzo-triazole | 0.1 | 45 |
| C | Base Fluid | + Example 1 | 0.1 | 70 |
| D | Base Fluid | + Example 2 | 0.1 | 70 |
| E | Base Fluid | + Example 3 | 0.1 | 70 |
| F | Base Fluid | + Example 4 | 0.1 | 70 |

As will be apparent from the foregoing table, the base fluid of Test A exhibited a load-support of only 45 load pounds per sq. in. The same base fluid with 0.1%, by weight, of benzotriazole showed no improvement. On the other hand, the same base fluid, by having incorporated therein 0.1 percent, by weight, of the specific reaction products of Examples 1 through 4, respectively, indicated improved and satisfactory results viz. 70 load pounds per sq. in.

While preferred embodiments of the compositions of the present invention, and specific benzotriazole derivatives, as corrosion inhibitors, have been described for purposes of illustration, it will be understood that various modifications and adaptations thereof, which will be obvious to those skilled in the art, may be made without departing from the spirit of the invention.

I claim:

1. A lubricant composition comprising a major proportion of an oil lubricating viscosity and greases thereof and normally susceptible of corroding copper, containing, in an amount sufficient to inhibit such corrosion, the reaction product of (A) benzotriazole and (B) a reactant selected from the group consisting of hydrocarbyl carboxylic acids having at least 18 carbon atoms, mono and di-substituted hydrocarbyl phosphates and mono and di-substituted organic phosphonates wherein the hydrocarbyl substituent contains at least 15 carbon atoms, and wherein said reaction is conducted at a temperature from about 100°C to about 200°C and in a mole ratio of (A) to (B) of from about 1:1 to about 1:0.5.

2. A composition in accordance with claim 1 wherein said composition comprises a gear oil.

3. A composition in accordance with claim 1 wherein said composition comprises a hydraulic oil.

4. A composition in accordance with claim 1 wherein said composition comprises a turbine oil.

5. A composition in accordance with claim 1 wherein said composition comprises a cutting oil.

6. A composition in accordance with claim 1 wherein said reaction product is present in an amount from about 0.001 to about 1 percent, by weight.

7. A composition in accordance with claim 1 wherein said reaction product is present in an amount from about 0.1 to about 0.5 percent, by weight.

8. A composition in accordance with claim 1 wherein said carboxylic acid comprises oleic acid.

9. A composition in accordance with claim 1 wherein said carboxylic acid comprises a dimer acid.

10. A composition in accordance with claim 1 wherein said carboxylic acid comprises a trimer acid.

11. A composition in accordance with claim 1 wherein said hydrocarbyl phosphate comprises a mono(nonylphenyl) phosphate.

12. A composition in accordance with claim 1 wherein said hydrocarbyl phosphate comprises a di(-nonylphenyl) phosphate.

13. A composition in accordance with claim 1 wherein said hydrocarbyl phosphonate comprises a mono(nonylphenyl) phosphonate.

14. A composition in accordance with claim 1 wherein said hydrocarbyl phosphonate comprises a di(nonylphenyl) phosphonate.

* * * * *